United States Patent [19]

Silver

[11] Patent Number: 5,003,993
[45] Date of Patent: Apr. 2, 1991

[54] METHOD AND APPARATUS FOR PREVENTING AND TREATING ANAEROBIC INFECTIONS

[76] Inventor: David R. Silver, 719 Washington St., Ste. 104, Newtonville, Mass. 02160

[21] Appl. No.: 453,598

[22] Filed: Dec. 20, 1989

[51] Int. Cl.$^5$ .......................... A61F 6/02; A61F 5/00
[52] U.S. Cl. ...................................... 128/842; 128/79
[58] Field of Search .............. 128/830, 831, 832, 833, 128/834, 837, 842, 844, 79; 604/347–353; 63/5.2

[56] References Cited

U.S. PATENT DOCUMENTS

| | | | |
|---|---|---|---|
| 178,458 | 6/1876 | Otto | 128/834 |
| 204,548 | 6/1878 | Durand | 63/5.2 |
| 328,553 | 10/1885 | Warnoth | 128/834 |
| 804,086 | 11/1905 | Barchfeld | 128/834 |
| 1,615,945 | 1/1927 | Janis | 128/79 |
| 1,627,255 | 5/1927 | Smith | 63/5.2 |
| 2,538,136 | 1/1951 | Twachtman | 128/844 |
| 3,612,057 | 10/1971 | Freedman | 128/303 |
| 4,139,007 | 2/1979 | Diamond | 128/842 |
| 4,760,715 | 8/1988 | Ramos, Jr. | 63/5.2 |
| 4,834,115 | 5/1989 | Stewart | 128/842 |

FOREIGN PATENT DOCUMENTS 8500470 9/1986 Netherlands ................ 128/832

*Primary Examiner*—Robert A. Hafer
*Assistant Examiner*—Michael Brown
*Attorney, Agent, or Firm*—Henry D. Pahl, Jr.

[57] ABSTRACT

In the method disclosed herein for preventing and treating anaerobic infectons in the region of the penile sulcus, a radially compliant ring, formed of a helically coiled resilient filament, is passed over the penile head and then seated in the sulcus behind the corona, the foreskin having been rolled back to expose the sulcus. The foreskin may then be released but is prevented from moving forward to cover the sulcus and penile head by the ring, thus allowing air to circulate in the region of the sulcus.

6 Claims, 1 Drawing Sheet

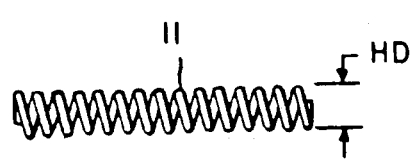
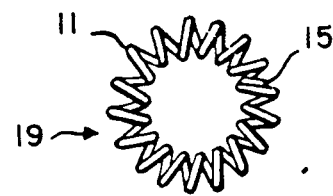
FIG.1  FIG.2
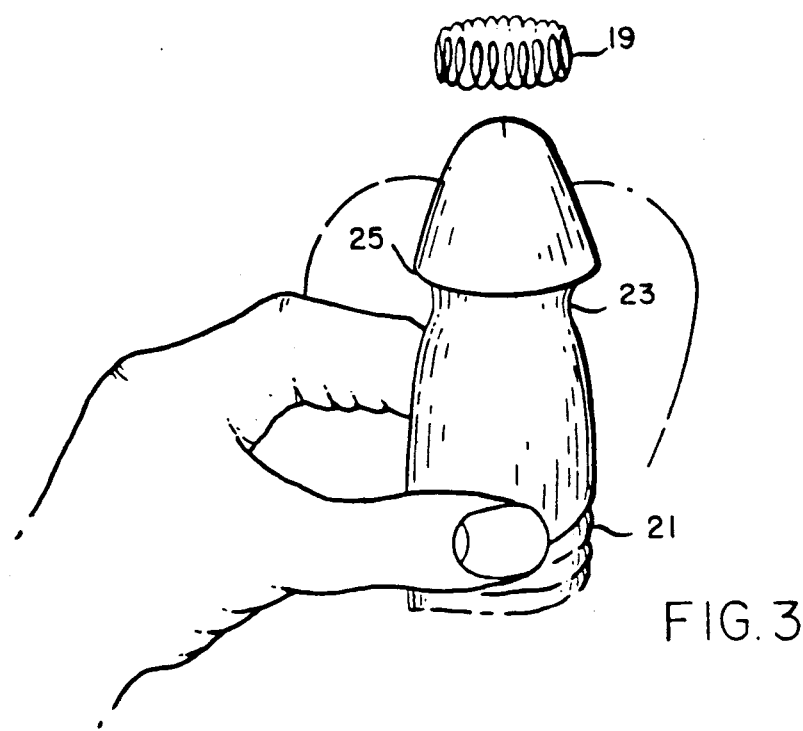
FIG.3
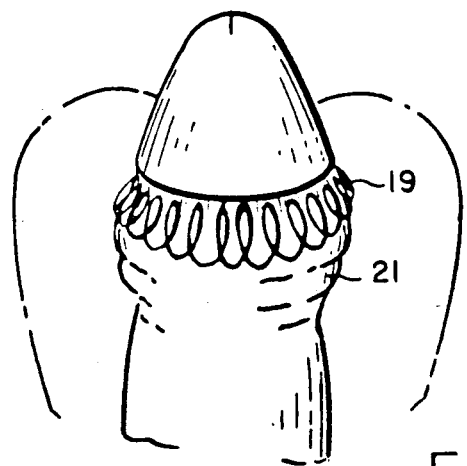
FIG.4

METHOD AND APPARATUS FOR PREVENTING AND TREATING ANAEROBIC INFECTIONS

BACKGROUND OF THE INVENTION

The present invention relates to a method and apparatus for preventing and treating anaerobic infections in the region of the penile sulcus in uncircumcized human males.

While the advantages and disadvantages of circumcizing infant males is a subject of continuing debate, it is understood that uncircumcized adult males may be somewhat more subject to certain infections in the region of the penile sulcus, i.e. the groove behind the penile corona. Very often the proposed treatment for such infections is to perform circumcision. However, for a variety of personal, religious and/or medical reasons, circumcision is not an acceptable procedure for many patients.

The infections which are of concern with respect to the present invention include monilia and certain other yeast infections which tend to proliferate in humid unexposed regions of the body and are often resistant to antibiotic treatment but which are essentially anaerobic. Such infections can, however, often be prevented or treated by exposing the region of the sulcus to air. However, the usual method of effecting such treatment is to tie back the foreskin which can be uncomfortable to the patient.

Among the several objects of the present invention may be noted the provision of a method for preventing and treating anaerobic infections in the region of the penile sulcus in uncircumcized males which avoid circumcision; the provision of such a method which treats such infections by allowing air to circulate in the region of the sulcus; the provision of such a method which involves minimal discomfort to the patient; the provision of such a method which does not require tying back of the foreskin; the provision of such a method which is effective and which is inexpensive and easily effected by the patient himself. Further objects include the provision of an apparatus for facilitating the prevention and treatment of anaerobic infections in the region of the sulcus in uncircumcized human males, an apparatus which is effective in exposing the region of the sulcus to a circulation of air, an apparatus which does not cause irritation, which is easily cleaned, which can be applied by the patient himself and which is of relatively simple and inexpensive construction. Other objects and features will be in part apparent and in part pointed out hereinafter.

SUMMARY OF THE INVENTION

The method of the present invention employs a radially compliant ring formed of a helically coiled filament formed into a toroidally shaped ring. The ring is applied by rolling back the foreskin to expose the sulcus, expanding the ring to pass it over the penile head and then seating it in the sulcus behind the head, and then releasing the foreskin against the ring which holds back the foreskin thereby allowing air to circulate in the region of the sulcus.

BRIEF DESCRIPTION OF THE DRAWINGS

FIG. 1 is a side view of a helically coiled resilient filament suitable for forming apparatus in accordance with the present invention;

FIG. 2 is a front view of a radially compliant ring formed by joining the ends of the helically coiled filament of FIG. 1;

FIG. 3 is a view showing the foreskin rolled back to expose the penile sulcus preparatory to applying the apparatus of the present invention; and FIG. 4 is a view of a radially compliant ring constructed in accordance with the present invention applied to the sulcus of an uncircumcized human male.

Corresponding reference characters indicate corresponding parts throughout the several views of the drawings.

DESCRIPTION OF THE PREFERRED EMBODIMENT

As indicated previously, the radially compliant ring of the present invention is formed by a helically coiled resilient filament. The ring may be fabricated integrally by injection molding into a suitable die or by joining the ends of length of helically coiled filament. A length of helically coiled filament, prior to being formed into a ring, is illustrated in FIG. 1. The filament itself is designated as reference character 11 while the helical diameter is designated as HD. A diameter of about one-quarter inch has been found appropriate for the purposes of the present invention. While a non-reactive metal might be used for the filament, the presently preferred material for the filament is a hard but resilient plastic resin such as nylon or polystyrene. A nominal filament diameter of about 0.045 inch is appropriate using such a plastic material.

To form a radially compliant ring suitable for the purposes of the present invention, the ends of the helically coiled filament are brought together and bonded, i.e. as designated by reference character 15 in FIG. 2. Bonding may be accomplished by the use of either an adhesive or by ultrasonic welding. The relaxed inner diameter of the ring so formed is about one-half inch, i.e. significantly smaller than the nominal diameter of the penile sulcus of an adult human male. The ring itself is designated by reference character 19.

To apply the ring, the penile foreskin, designated by reference character 21, is manually rolled back as illustrated in FIG. 3 to expose the sulcus, designated by reference character 23. The ring 19 is then expanded to pass it over the corona of the penile head, designated by reference character 25, and is then seated in the sulcus behind the corona. Once the ring is seated in the sulcus, the foreskin is then released against the ring, as illustrated in FIG. 4, so that the ring holds back the foreskin preventing it from moving forward, thereby leaving the sulcus and penile head exposed to the circulation of fresh air.

Since the ring 19 is expanded in application, a majority of the surface of the sulcus is in fact exposed to air by this means. In other words, the portion of the sulcus surface which is actually in contact with the filament material is quite small. Further, normal human motions will cause the points of contact to shift so that virtually all portions of the sulcus will enjoy the benefit of the ventilation provided. Since a ring constructed of a helix is inherently quite compliant in the radial direction, there is very little constricting force and thus the patient experiences minimal discomfort from this force. Further, although the foreskin is somewhat retracted by the presence of the ring, there is not nearly the discomfort as is associated with a complete tying back of the foreskin as has been proposed in some earlier treatments.

An advantage of the method and apparatus of the present invention is that the ring 19 can easily be applied by the patient himself and likewise can be cleaned and maintained without any special facilities. Although the ring 19 constitutes a very open and airy structure in one sense thereby faciliitating the free circulation of air around the sulcus region, the filament itself, being a hard non-porous material, is easily cleaned and sterilized and does not tend to retain dirt and mucous as would a sponge-like material as has been proposed in the prior art. For example, sterilization may be effected by commonly available peroxide solutions.

In view of the foregoing, it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

What is claimed is:

1. The method of preventing and treating anaerobic infections in the region of the sulcus in uncircumcized human males, said method comprising:
   rolling back the foreskin;
   providing a radially compliant ring formed of a helically coiled resilient filament of a hard, non-porous material, the relaxed inner diameter of said ring being less than the nominal diameter of the sulcus;
   expanding said ring to pass it over the penile head and then seating it in the sulcus behind said head;
   releasing the foreskin against said ring thereby allowing air to circulate in the region of the sulcus.

2. The method of preventing and treating anaerobic infections in the region of the sulcus in uncircumcized human males, said method comprising:
   providing a helically coiled filament of a hard, non-porous and resilient material;
   bringing the ends of said filament together and bonding them thereby to form a toroidally shaped ring, the relaxed inner diameter of said ring being less than the nominal diameter of the sulcus;
   rolling back the foreskin;
   expanding said ring to pass it over the penile head and then seating it in the sulcus behind said head;
   releasing the foreskin against said ring thereby allowing air to circulate in the region of the sulcus.

3. The method of claim 2 wherein the helical diameter is about one-quarter inch.

4. The method of claim 2 wherein said relaxed inner diameter of said ring is about one-half inch.

5. The method of claim 2 wherein said material is a plastic resin.

6. The method of preventing or treating anaerobic infections in the region of the sulcus in an uncircumcized human male patient, said method comprising:
   providing a filament of a hard, non-porous and resilient plastic resin material helically coiled with a diameter of about one-quarter inch and formed into a toroidally shaped ring, the relaxed inner diameter of said ring being about one-half inch;
   rolling back the foreskin of the patient to expose the sulcus;
   expanding said ring to pass it over the penile head and then seating it in the sulcus behind said head;
   releasing the foreskin against said ring thereby allowing air to circulate in the region of the sulcus.

* * * * *